(12) United States Patent
Ishikawa et al.

(10) Patent No.: US 9,976,990 B2
(45) Date of Patent: May 22, 2018

(54) VIBRATION MEASURING APPARATUS USING PARAMETRIC SPEAKER AND TWO-DIMENSIONAL SCANNING MIRROR

(71) Applicant: TOSHIBA TEC KABUSHIKI KAISHA, Shinagawa-ku, Tokyo (JP)

(72) Inventors: Daisuke Ishikawa, Shizuoka (JP); Kenichi Komiya, Kanagawa (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 190 days.

(21) Appl. No.: 14/980,096

(22) Filed: Dec. 28, 2015

(65) Prior Publication Data

US 2016/0202215 A1    Jul. 14, 2016

(30) Foreign Application Priority Data

Jan. 14, 2015    (JP) .................................. 2015-004958

(51) Int. Cl.
*G01N 29/24*    (2006.01)
*G01N 29/11*    (2006.01)
*G01N 21/17*    (2006.01)

(52) U.S. Cl.
CPC ..... *G01N 29/2418* (2013.01); *G01N 21/1702* (2013.01); *G01N 29/11* (2013.01); *G01N 2291/017* (2013.01)

(58) Field of Classification Search
CPC ............... G01N 29/11; G01N 29/2418; G01N 2291/017
See application file for complete search history.

(56) References Cited

U.S. PATENT DOCUMENTS

| 2003/0016434 | A1* | 1/2003 | Torchigin ................ G02F 1/125 |
| | | | 359/286 |
| 2016/0157820 | A1* | 6/2016 | Han ........................ A61B 8/15 |
| | | | 600/459 |
| 2017/0212084 | A1* | 7/2017 | Komiya .................. G01N 29/07 |

FOREIGN PATENT DOCUMENTS

| JP | 2005-315793 | 11/2005 |
| JP | 2012-127897 | 7/2012 |
| JP | 2012-237561 | 12/2012 |

(Continued)

OTHER PUBLICATIONS

Machine translation of JP2014-106102.*

(Continued)

*Primary Examiner* — Natalie Huls
(74) *Attorney, Agent, or Firm* — Amin, Turocy & Watson LLP

(57) ABSTRACT

A vibration measuring apparatus comprises a wave transmission section configured to vibrate a measurement object with sound wave output from a parametric speaker towards the measurement object and an optical measurement section configured to emit laser light towards the measurement object, receive the laser light reflected from the measurement object and measure vibration of the assumed object (measurement object) according to the received laser light. The wave transmission section and the optical measurement section are mounted integrally, and the optical measurement section makes an optical axis of laser light emitted to/received from the measurement object coincident with a central axis of the sound wave output from the parametric speaker.

17 Claims, 8 Drawing Sheets

(56) References Cited

FOREIGN PATENT DOCUMENTS

JP          2014-106102          6/2014

OTHER PUBLICATIONS

Machine translation of JP2012-127897.*
Machine translation of JP2005-315793.*
Japanese Office Action for Japanese Patent Application No. 2015-004958 dated Jun. 27, 2017.

* cited by examiner

VIBRATION MEASURING APPARATUS USING PARAMETRIC SPEAKER AND TWO-DIMENSIONAL SCANNING MIRROR

CROSS-REFERENCE TO RELATED APPLICATION

This application is based upon and claims the benefit of priority from Japanese Patent Application No. P2015-004958, filed Jan. 14, 2015, the entire contents of which are incorporated herein by reference.

FIELD

Embodiments described herein relate generally to a vibration measuring apparatus for measuring vibration with the use of a laser Doppler principle.

BACKGROUND

In recent years, the measurement of tiny vibration amplitude is becoming possible with the user of a laser Doppler principle in a non-contact manner. In the laser Doppler principle, Doppler shift occurs in scattering light if a vibrating object is irradiated with laser light. Information such as vibration amplitude generated in the object can be obtained by observing light beat (interference) between the scattering light and reference light.

A detection method is proposed which applies vibration to a detection object actively and grasps a state of the object by observing the vibration of the object with the use of the laser Doppler principle (see Japanese Unexamined Patent Application Publication No. 2012-237561).

On the other hand, a technology is proposed which vibrates an object with the sound wave having a sharp directivity by using ultrasonic wave like a parametric speaker as a module that vibrates an object in a non-contact manner (see Japanese Unexamined Patent Application Publication No. 2014-106102).

The technology disclosed in Japanese Unexamined Patent Application Publication No. 2014-106102 comprises a wave transmission section for outputting sound wave towards an object and an optical measurement section for optically measuring vibration. The wave transmission section and the optical measurement section are arranged at optional positions for use (physical positions thereof are different from each other). Thus, it is necessary to re-adjust an angle of the wave transmission section according to a distance and an angle between the optical measurement section and a measurement object. It takes much time and effort to obtain lots of data and to realize normalization.

DETAILED DESCRIPTION

A vibration measuring apparatus for realizing an purpose of an embodiment comprises a wave transmission section configured to vibrate a measurement object with sound wave output from a parametric speaker towards the measurement object and an optical measurement section configured to emit laser light towards the measurement object, receive the laser light reflected from the measurement object and measure vibration of the assumed object (measurement object) according to the received laser light. The wave transmission section and the optical measurement section are mounted integrally, and the optical measurement section makes an optical axis of laser light emitted to/received from the measurement object coincident with a central axis of the sound wave output from the parametric speaker.

A vibration measuring apparatus is described hereinafter, with reference to the accompanying drawings.

First Embodiment

Figure 1:
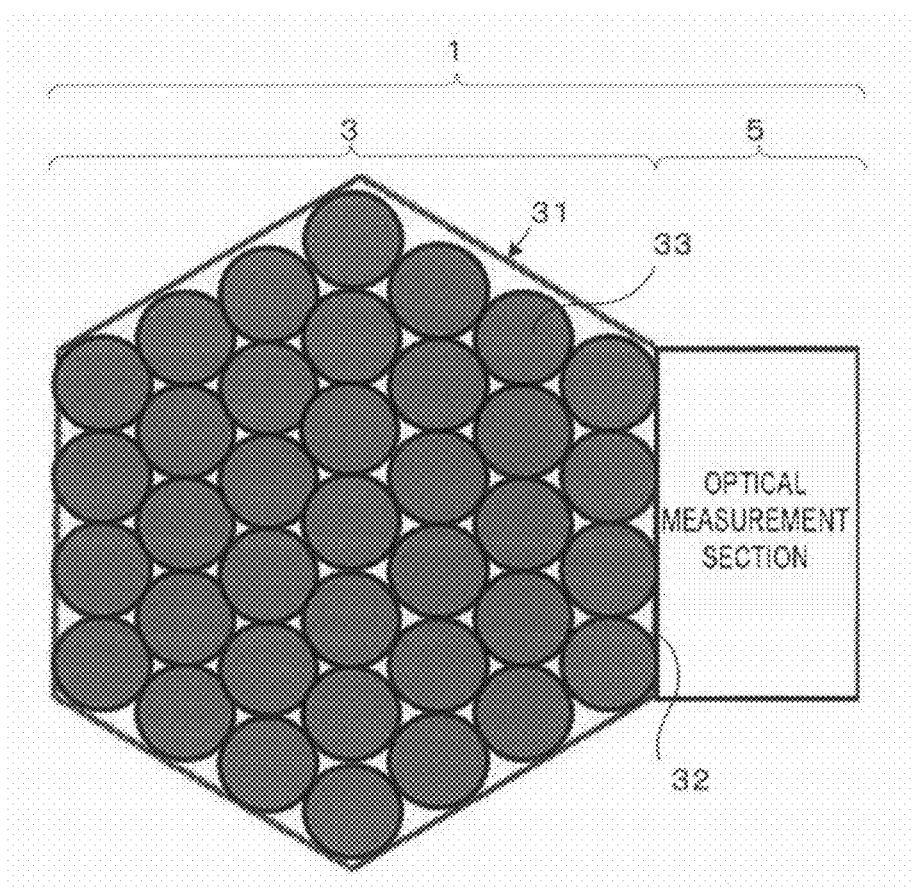
FIG. 1 is a front view schematically illustrating a vibration measuring apparatus according to a first embodiment.
Figure 2:
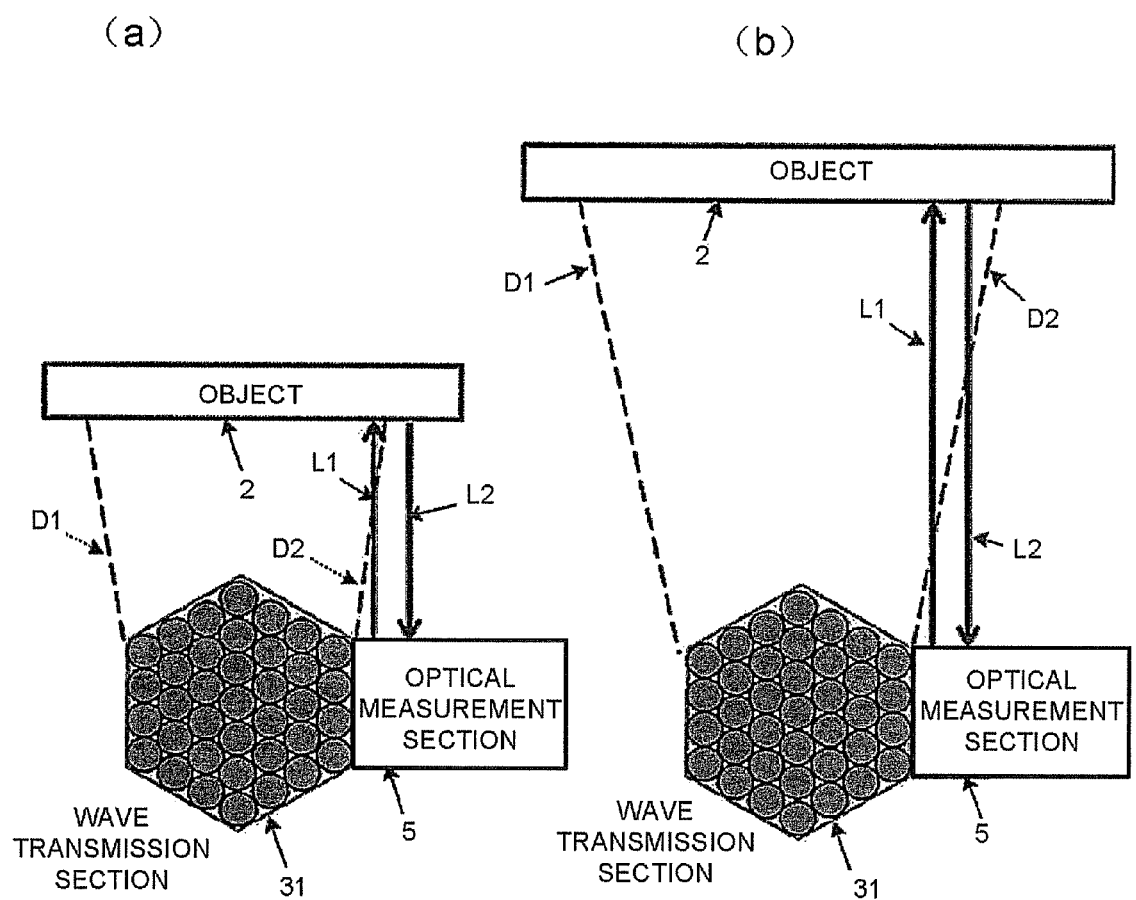
FIG. 2 is a diagram illustrating a vibration measuring method by the vibration measuring apparatus shown in FIG. 1.
Figure 3:
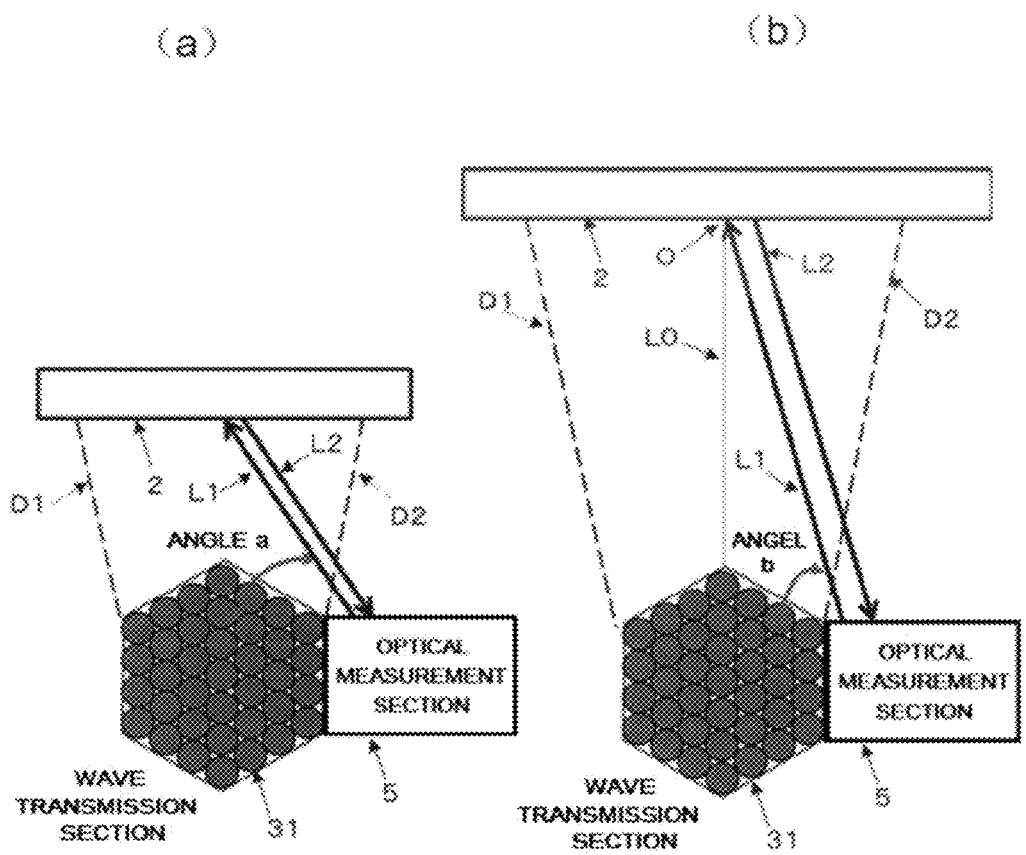
FIG. 3 is a diagram illustrating a deficient vibration measuring method.
Figure 4:
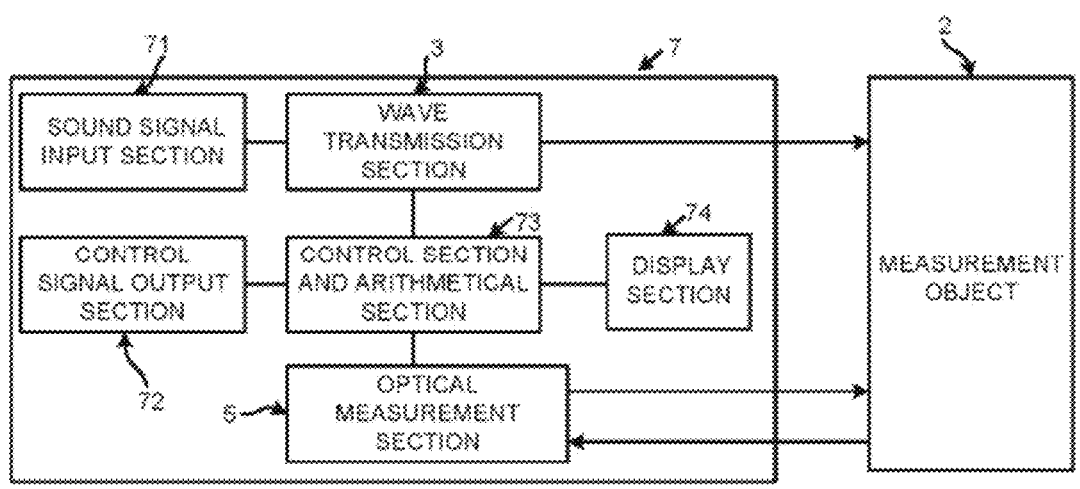
FIG. 4 is a circuit block diagram of the vibration measuring apparatus.
Figure 5:
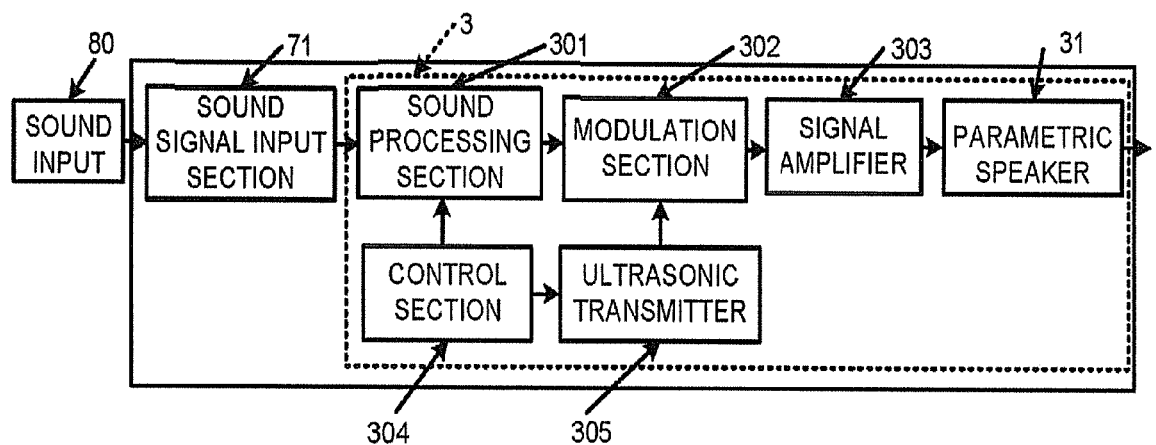
FIG. 5 is a circuit block diagram of a wave transmission section shown in FIG. 4.
Figure 6:
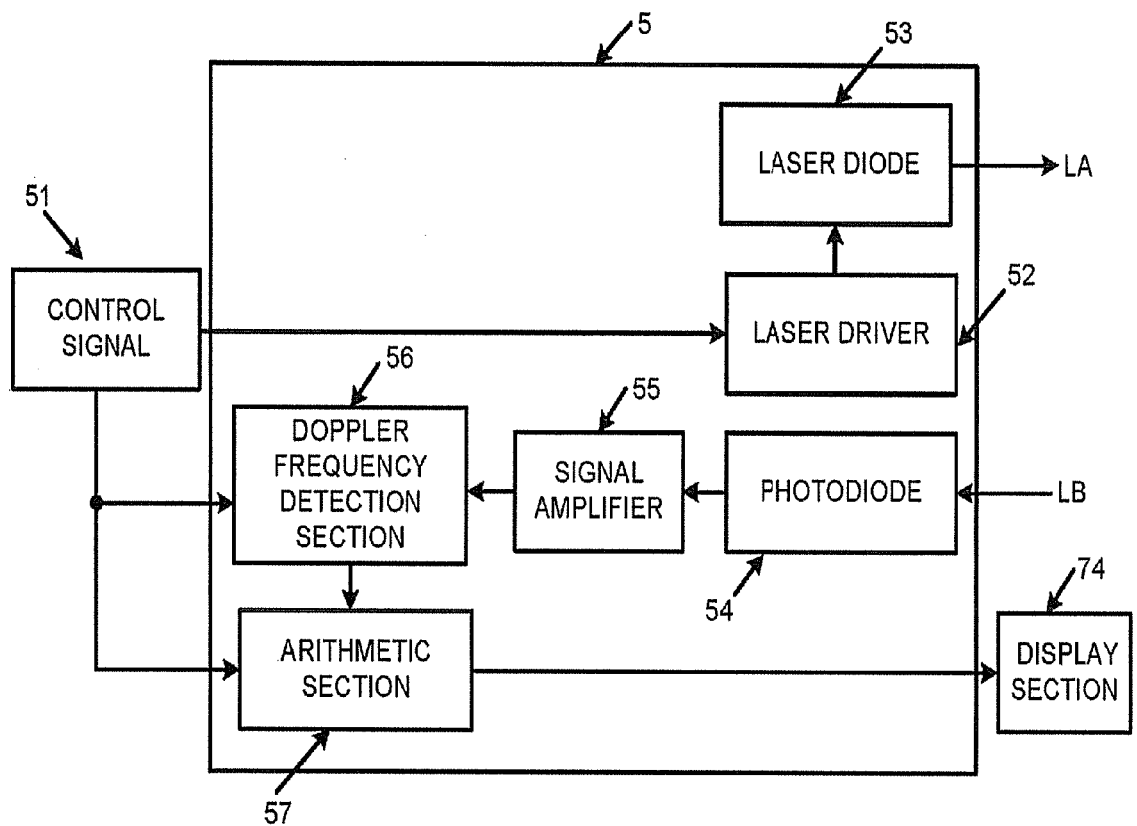
FIG. 6 is a circuit block diagram of an optical measurement section shown in FIG. 4.
Figure 7:
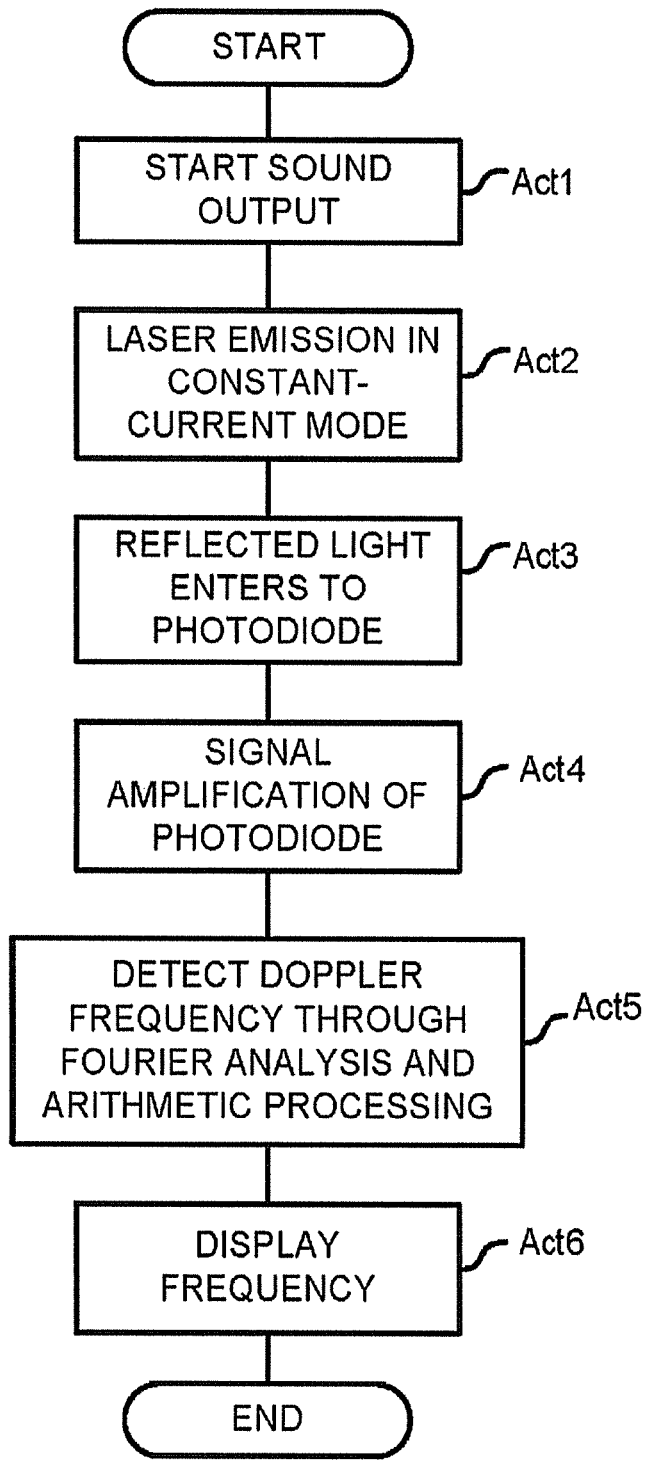
FIG. 7 is a flowchart illustrating the operation of the vibration measuring apparatus shown in FIG. 4.

FIG. 1 is a front view schematically illustrating the vibration measuring apparatus according to the first embodiment. FIG. 2 is a diagram illustrating a first vibration measuring method by the vibration measuring apparatus shown in FIG. 1. FIG. 3 is a diagram illustrating a second vibration measuring method by the vibration measuring apparatus shown in FIG. 1. FIG. 4 is a circuit block diagram illustrating a driving section arranged in the vibration measuring apparatus. FIG. 5 is a circuit block diagram of the wave transmission section shown in FIG. 4. FIG. 6 is a circuit block diagram of the optical measurement section shown in FIG. 4. FIG. 7 is a flowchart illustrating the operation of the vibration measuring apparatus shown in FIG. 4;

In FIG. 1, a vibration measuring apparatus 1 is provided with a wave transmission section 3, an optical measurement section 5 and a driving section 7 (refer to FIG. 4) for driving the wave transmission section 3 and the optical measurement section 5.

The wave transmission section 3 includes a parametric speaker 31 and transmits ultrasonic wave with a high directivity from the parametric speaker 31 forwards. The parametric speaker 31 of the wave transmission section 3 is arranged with a plurality of ultrasonic vibrators 32 densely into a plane surface of, for example, a regular hexagon. The shape of the plane surface which is not limited to the regular hexagon may be other polygons or a circular shape such as perfect circular shape or elliptical shape.

The optical measurement section 5 measures tiny vibration amplitude generated in a measurement object in a non-contact manner with the user of a laser Doppler principle. In the laser Doppler principle, if laser light is emitted to a vibrating measurement object, Doppler shift occurs in scattering light reflected from the measurement object. Information such as vibration amplitude generated in the measurement object is obtained by observing beat of light (interference) between the scattering light and reference light.

When a wave of light reflected from the vibrating measurement object is measured, the frequency shift of the measured waves is indicated by $(2 \cdot V)/\lambda$, wherein, V is a speed of vibration generated in the vibrating measurement object and $\lambda$ is a wave length of the emitted light.

In the present embodiment, the wave transmission section 3 is used as a module for vibrating the measurement object in a non-contact manner. The wave transmission section 3 causes the sound wave from the parametric speaker 31 in the area of the ultrasonic wave to have a sharp directivity to vibrate the measurement object, and at the same time, the vibration of the vibrating measurement object is optically measured by the optical measurement section 5. The sound wave output from the parametric speaker 31 of the wave transmission section 3 of frequency in an ultrasonic wave area is added with, for example, a sound wave of frequency in an audible range. The sound wave in the audible range frequency possesses large energy, and thus is capable of vibrating the measurement object.

In the present embodiment, the optical measurement section 5 is integrally fixed on a side surface 33 of the parametric speaker 31 of the wave transmission section 3. Owing to the integrated structure, even if a location where vibration of the measurement object is measured is different from a target location, the measurement of the vibration can be carried out simply without adjusting the positions of the wave transmission section 3 and the optical measurement section 5.

Distances between a measurement object 2 and the vibration measuring apparatus 1 shown in FIGS. 2 (a) and (b) are different from that shown in FIGS. 3 (a) and (b). FIGS. 2 (a) and (b) and FIGS. 3 (a) and (b) are diagrams facing upper surface to show a speaker surface of the parametric speaker 31 of the wave transmission section 3; however, they face the measurement object 2 side actually. A laser emitting surface of the optical measurement section 5 and a light receiving surface receiving laser light reflected from the measurement object 2 face the measurement object 2 side actually.

FIGS. 2 (a) and (b) show a case in which laser light from the optical measurement section 5 is emitted to the measurement object 2 at a right angle. In FIG. 2 (a) and FIG. 2 (b), a range of directivity which the ultrasonic wave output from the wave transmission section 3 can reach is within a range composed of dotted lines D1 and D2. As shown in FIG. 2 (a), a distance between the vibration measuring apparatus 1 and the measurement object 2 facing each other is short, the laser light emitted from the optical measurement section 5 to the measurement object 2 is located at the end of the directivity which the ultrasonic wave can reach. As shown in FIG. 2 (b), the distance between the vibration measuring apparatus 1 and the measurement object 2 facing each other is long, the laser light emitted from the optical measurement section 5 to the measurement object 2 exists in the range of the directivity which the ultrasonic wave can reach.

Thus, in FIG. 2 (a) and FIG. 2 (b), the laser light from the optical measurement section 5 is emitted to the same position of the measurement object 2. However, conditions, that is, vibration conditions caused each time the ultrasonic wave output from the wave transmission section 3 impinges on the position to which the laser light is emitted are different from one another, and thus it is difficult to obtain a stable reproducibility.

On the contrary, as shown in FIGS. 3 (a) and (b), similarly to FIGS. 2 (a) and (b), in a case of outputting the ultrasonic wave from the wave transmission section 3 to the measurement object 2, an emitting optical axis L1 of the laser light from the optical measurement section 5 and an incident optical axis L2 of a light receiving section change along with the change of angle a and angle b. The center of the sound wave output from the wave transmission section 3 to the measurement object 2 is regarded as L0.

The angle a and angle b are both used to make the emitting optical axis L1 and the incident optical axis L2 of the laser light coincident with a center point O where the center L0 of the sound wave hits on the measurement object 2. A mechanism is exemplified to adjust an angle with the emitting optical axis L1 of the laser light of the optical measurement section 5 and an angle with the incident optical axis L2 of the light receiving section through a two-dimensional scanning mirror as a module of changing the emitting optical axis L1 of the laser light of the optical measurement section 5 and the incident optical axis L2 of the light receiving section along with the change of the angle a and angle b.

A method of emitting a laser pointer to the center point O can be presented as a method of making the emitting optical axis L1 of the laser light coincident with the center point O where the center L0 of the sound wave hits on the measurement object 2. In this method, the emitting optical axis L1 of the laser light is positioned at a position indicated by the laser pointer.

Thus, whether the distance between the vibration measuring apparatus 1 and the measurement object 2 is long or short, the emitting optical axis L1 and the incident optical axis L2 can be coincident with the center point O where the center L0 of the sound wave hits on the measurement object 2, thereby measuring the vibration generated in the measurement object stably.

The driving section 7 of the vibration measuring apparatus 1, as shown in FIG. 4, includes a sound signal input section 71, a control signal output section 72, a control section and arithmetical section 73 and a display section 74. The sound signal input section 71 outputs, for example, a signal (sound signal) of frequency in the audible range to the wave transmission section 3. The control section and arithmetical section 73 carries out the control and the calculation of the wave transmission section 3 and the optical measurement section 5 according to a control signal input to the control signal output section 72 and the result thereof is displayed on the display section 74.

The wave transmission section 3, as shown in FIG. 5, includes a sound processing section 301 for processing the sound signal of the audible range frequency from the sound signal input section 71, a modulation section 302 for modulating ultrasonic wave frequency from a ultrasonic transmitter 305 by adding the sound signal from the sound processing section 301 in the ultrasonic wave frequency, a control section 304 for controlling output timings of the sound processing section 301 and the ultrasonic transmitter 305, a signal amplifier 303 for amplifying the output of the modulation section 302 and the parametric speaker 31 to which the ultrasonic wave signal amplified by the signal amplifier 303 is input. The sound (audible range frequency) signal is input to the sound signal input section 71 from a sound input section 80. Modification signal output from the modulation section 302 includes both the high directivity and the large amplitude.

The optical measurement section 5, as shown in FIG. 6, includes a laser driver 52 to which a control signal 51 is input, a laser diode 53, driven by the laser driver 52, which emits a laser light LA to the measurement object, a photodiode 54 for receiving a reflected light LB reflected from the measurement object, a signal amplifier 55 for amplifying reception signal obtained by receiving the reflected light LB by the photodiode 54, a Doppler frequency detection section 56 to which the signal amplified by the signal amplifier 55 is input and an arithmetic section 57 for calculating vibration data, speed data and displacement data according to vibration component detected by the Doppler frequency detection section 56. Various data calculated by the arithmetic section 57 is displayed on the display section 74.

Operations of the vibration measuring apparatus 1 are described on the basis of a flowchart shown in FIG. 7.

If the present processing is started, in Act 1, sound wave from the parametric speaker 31 of the wave transmission section 3 is emitted to the measurement object 2 to vibrate the measurement object 2, and then the processing in Act 2 is carried out.

In Act 2, the laser diode 53 for measurement of the optical measurement section 5 is driven to, enable a laser to emit light to the measurement object 2 in a constant-current mode, and then the processing in Act 3 is carried out.

In Act 3, the reflected light LB from the measurement object 2 is received by the photodiode 54, and then the processing in Act 4 is carried out.

In Act 4, after a signal of tint electric current flowing in the photodiode 54 is converted into a voltage signal, the signal is amplified by the signal amplifier 55, and then the processing in Act 5 is carried out.

In Act 5, the signal amplified by the signal amplifier 55 is detected by the Doppler frequency detection section 56 through Fourier analysis and further an arithmetic processing is carried out by the arithmetic section 57 to extract the vibration component to calculate the vibration data, the speed data and the displacement data, and then the processing in Act 6 is carried out.

In Act 6, the vibration data, the speed data and the displacement data are displayed on the display section 74.

Second Embodiment

Figure 8:
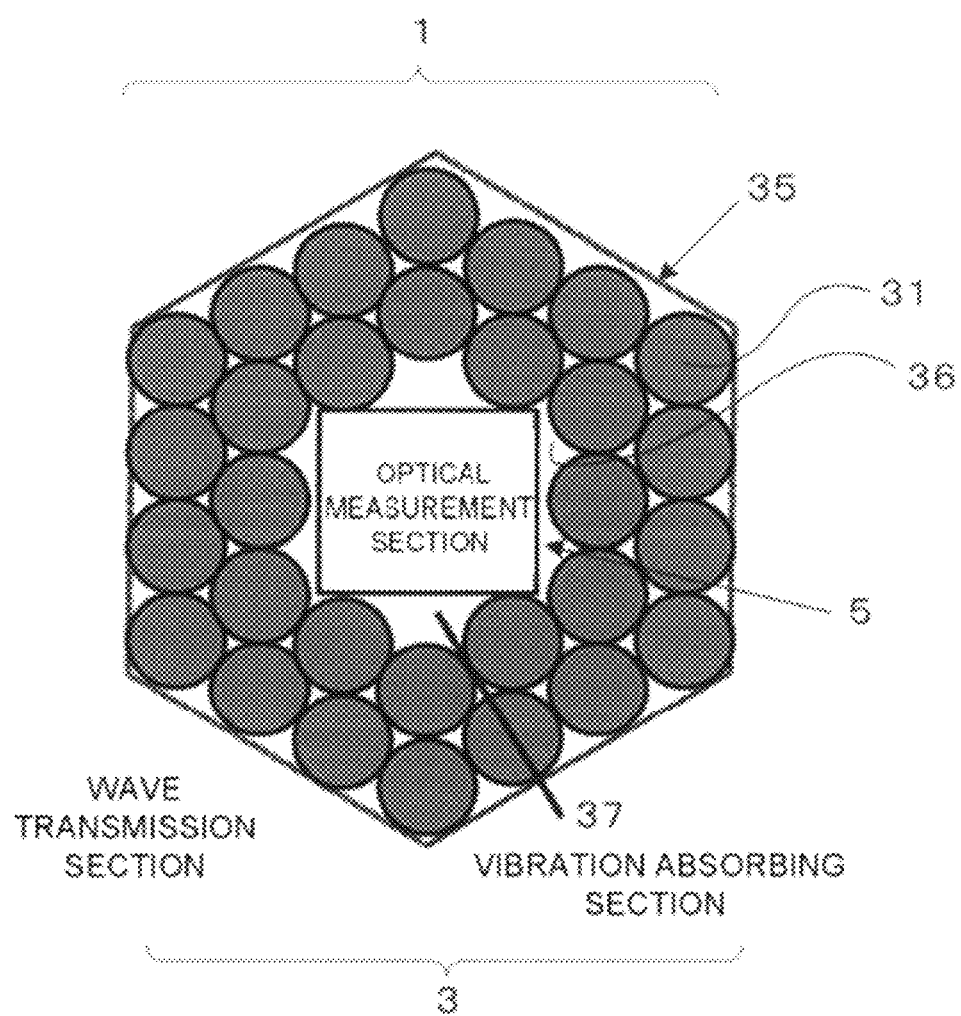
FIG. 8 is a front view schematically illustrating a vibration measuring apparatus according to a second embodiment.
Figure 9:
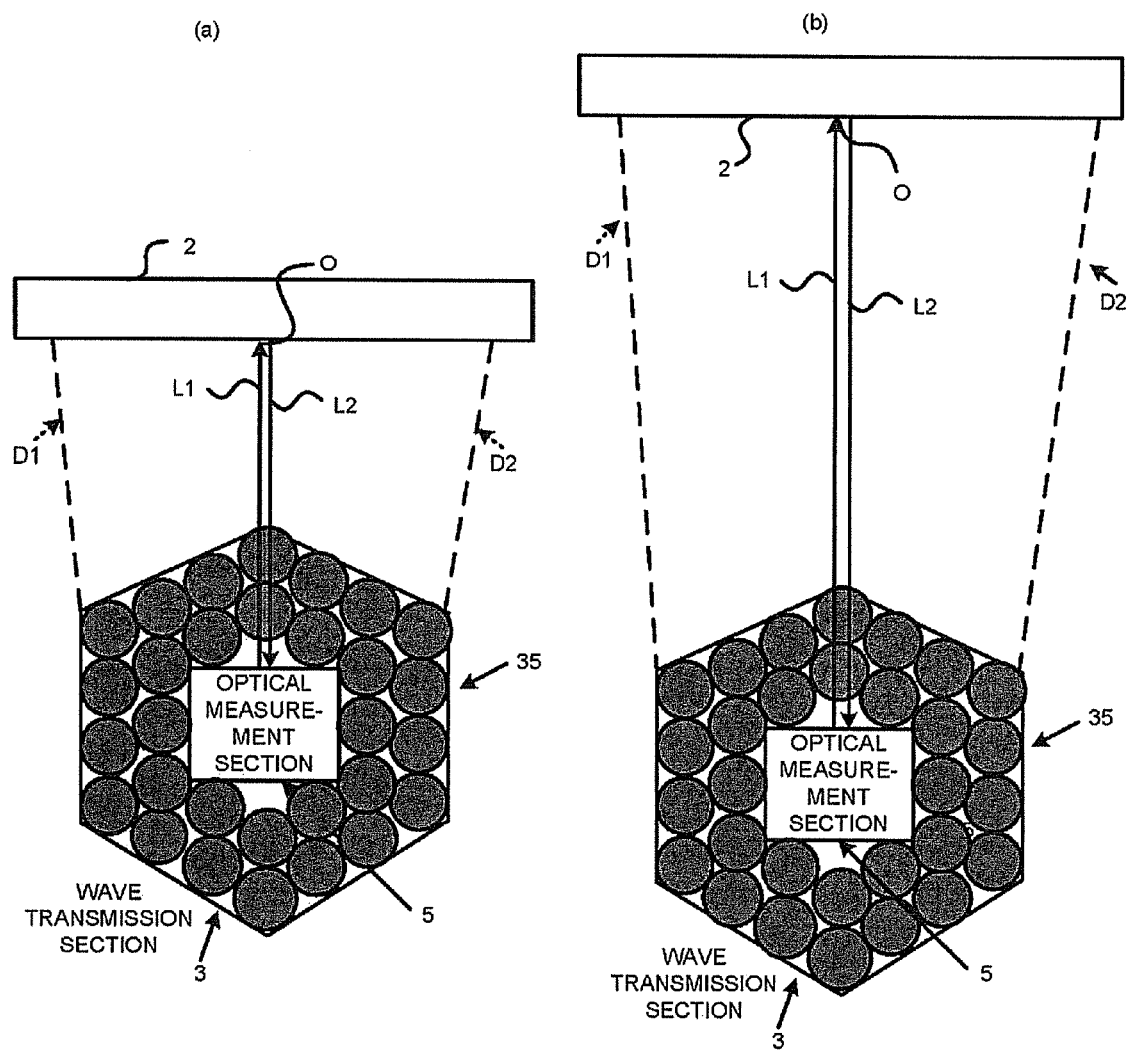
FIG. 9 is a diagram illustrating a vibration measuring method by the vibration measuring apparatus shown in FIG. 8.

FIG. 8 is a front view schematically illustrating a vibration measuring apparatus according to the second embodiment. FIG. 9 is a diagram illustrating a vibration measuring method of the vibration measuring apparatus shown in FIG. 8.

The vibration measuring apparatus 1 of the second embodiment arranges the optical measurement section 5 in an empty space section 36 that is arranged at the center part of a parametric speaker 35 of the wave transmission section 3. The parametric speaker 35 of the present embodiment is arranged with a plurality of ultrasonic vibrators 32 closely excluding the empty space section 36 that is arranged at the center part of a hexagon plane. The optical measurement section 5 is held in the empty space section 36 via a vibration absorbing section 37 which absorbs vibration generated by the parametric speaker 35. Thus, the vibration generated by the parametric speaker 35 cannot be transmitted to the optical measurement section 5 and the vibration can be measured with a high degree of accuracy.

In the present embodiment, the center of the output of the sound wave of the wave transmission section 3 and the emitting optical axis and the incident optical axis of the laser light of the optical measurement section 5 are arranged integrally on the same axial line. That is, the emitting optical axis L1 of the optical measurement section 5 is coincident with the center point O where the sound wave output from the parametric speaker 35 is emitted to the measurement object 2.

Thus, as shown in FIGS. 9 (*a*) and (*b*), whether the distance between the measurement object 2 and the vibration measuring apparatus 1 facing each other is short or long, the emitting optical axis L1 and the incident optical axis L2 are always gathered on the center O of the wave transmission section 3, and thus vibration of the object can be measured.

Third Embodiment

Figure 10:
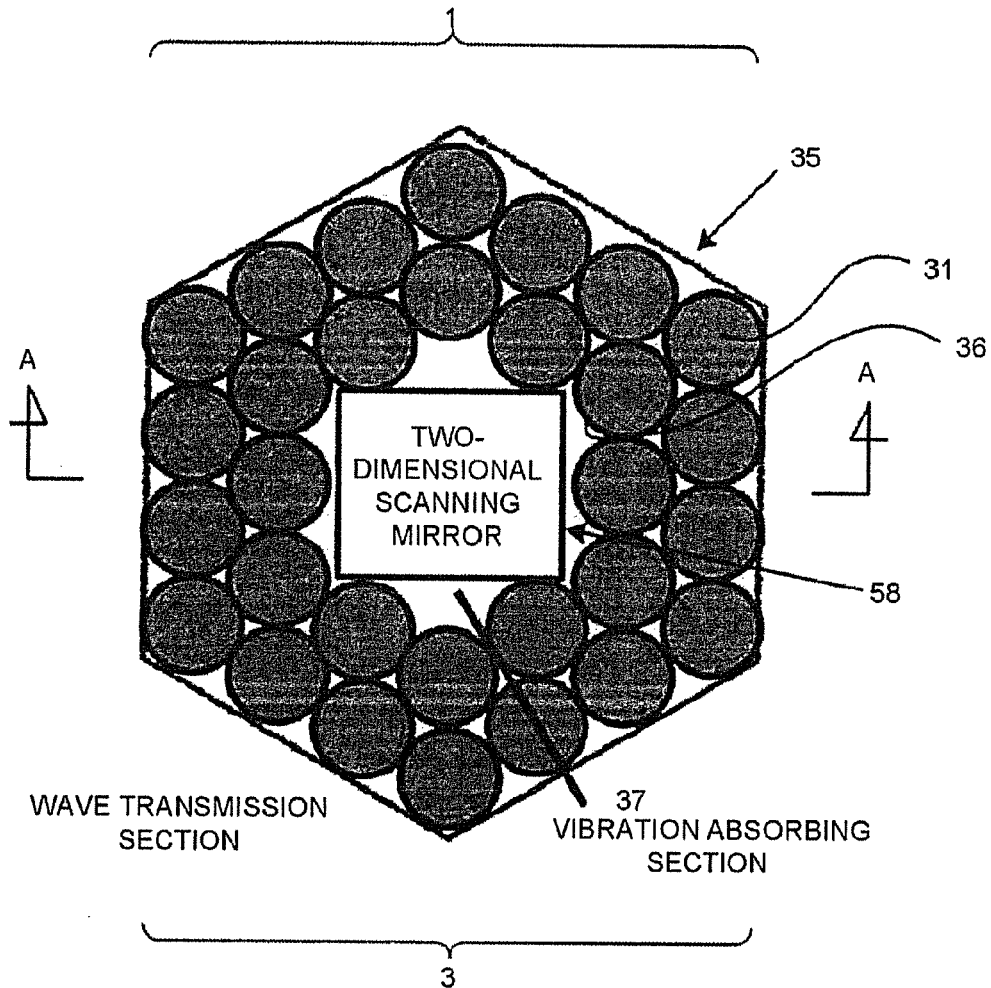
FIG. 10 is a front view schematically illustrating a vibration measuring apparatus according to a third embodiment.
Figure 11:
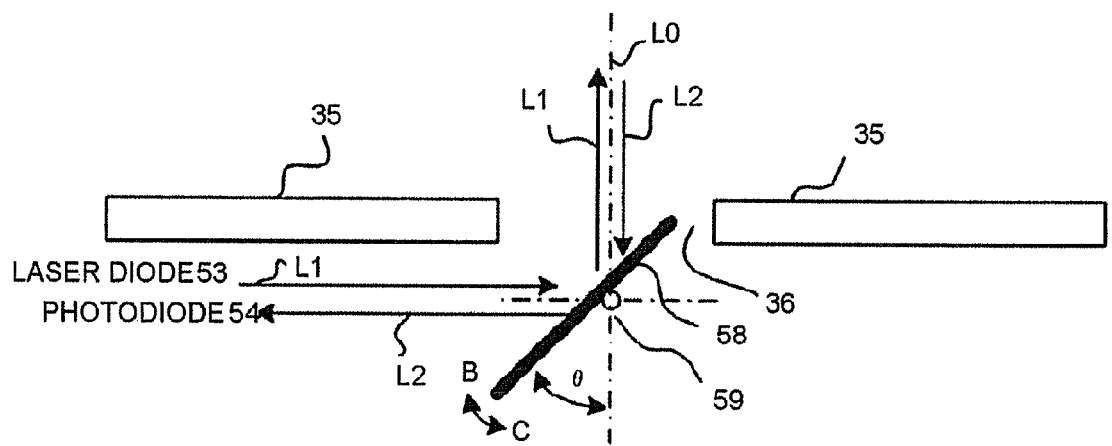
FIG. 11 is a visual cross-sectional view taken along an A-A line shown in FIG. 10.

FIG. 10 is a front view schematically illustrating a vibration measuring apparatus according to the third embodiment. FIG. 11 is visual cross-sectional view taken along an A-A line shown in FIG. 10.

The present embodiment is the modification of the second embodiment.

In the second embodiment shown in FIG. 8, the optical measurement section 5 is arranged in the empty space section 36 that is arranged at the center part of the parametric speaker 35 of the wave transmission section 3. On the contrary, in the present embodiment, a two-dimensional scanning mirror 58 is arranged in the empty space section 36.

The two-dimensional scanning mirror 58 can rotate around a fulcrum shaft 59 in the directions shown by arrows B and C to be capable of maintaining an optional rotational angle θ. The laser light from the laser diode 53 is emitted towards the two-dimensional scanning mirror 58. FIG. 11 shows a case in which the optional rotational angle 9 of the two-dimensional scanning mirror 58 is 45 degrees, and the emitting optical axis L1 of the laser light reflected by the two-dimensional scanning mirror 58 is coincident with the center line L0 of the parametric speaker 35.

The vibration in the vibration range of the parametric speaker 35 of the measurement object 2 can be measured by changing the optional rotational angle θ of the two-dimensional scanning mirror 58 and meanwhile transmitting/receiving the laser light.

That is, as it is arranged that the center of an one-dimensional or two-dimensional scanning mirror 58 serving as a scanning mechanism arranged in the optical measurement section approaches to the center of the parametric speaker 35 of the wave transmission section 3, even if the measurement object 2 is measured two-dimensionally, the scanning mirror 58 takes the center of the wave transmission section 3 as a starting point to carry out a scanning operation, and thus, distance and direction of a sound source with respect to the measurement object 2 is not limited, thereby carrying out a stable measurement.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

What is claimed is:

1. A vibration measuring apparatus, comprising:
 a wave transmission section configured to vibrate a measurement object with sound wave output from a parametric speaker towards the measurement object; and
 an optical measurement section configured to emit laser light towards the measurement object, receive the laser light reflected from the measurement object and measure vibration of the measurement object according to the received laser light, wherein the wave transmission section and the optical measurement section are mounted integrally, and the optical measurement section makes an optical axis of laser light emitted to/received from the measurement object coincident with a central axis of the sound wave output from the parametric speaker, and a two-dimensional scanning mirror used to reflect the laser light from the optical measurement section towards the measurement object and reflect the laser light reflected from the measurement object towards the optical measurement section that is arranged at the center part of the sound wave output from the parametric speaker.

2. The vibration measuring apparatus according to claim 1, wherein the parametric speaker is arranged with a plurality of ultrasonic vibrators closely excluding an empty space section that is arranged at the center part of a polygon plane.

3. The vibration measuring apparatus according to claim 2, wherein the polygon plane is regular hexagon plane.

4. The vibration measuring apparatus according to claim 2, wherein the two-dimensional scanning mirror is held in the empty space section via a vibration absorbing section which absorbs vibration generated by the ultrasonic vibrators.

5. The vibration measuring apparatus according to claim 1, wherein the optical measurement section comprises;

a laser light source configured to emit laser light; and
a light receiving element configured to receive the laser light reflected from the measurement object, and
the two-dimensional scanning mirror reflects the laser light from the laser light source towards the measurement object and reflects the laser light reflected from the measurement object towards a light receiving element side.

6. The vibration measuring apparatus according to claim 5, wherein the optical measurement section further comprises:

a signal amplifier configured to amplify the signal output from the light receiving element;
a Doppler frequency detection section configured to detect a Doppler frequency from the signal amplified by the signal amplifier; and
an arithmetic section configured to display vibration data on a display based on the Doppler frequency.

7. The vibration measuring apparatus according to claim 5, wherein the parametric speaker is arranged with a plurality of ultrasonic vibrators closely excluding the empty space section that is arranged at the center part of a polygon plane or a circular plane, the two-dimensional scanning mirror is held in the empty space section and is at a position deviated with respect to the ultrasonic vibrators in the direction orthogonal to the ultrasonic vibrators,
the two-dimensional scanning mirror reflects the laser light from the laser light source in the direction parallel to the ultrasonic vibrators towards the measurement object through the empty space section.

8. The vibration measuring apparatus according to claim 7, wherein the two-dimensional scanning is tilted at 45 degrees to the polygon plane.

9. A vibration measuring apparatus, comprising: an optical measurement section configured to comprise a laser light source configured to emit laser light, a light receiving element configured to receive the laser light output from the laser light source and reflected from the measurement object, and a two-dimensional scanning mirror used to reflect the laser light from the laser light source towards the measurement object and reflect the laser light reflected from the measurement object towards the light receiving element, and configured to measure vibration of the measurement object according to the received laser light; and a wave transmission section configured to comprise a plurality of vibrate sections, the vibrate sections which are arranged around the two-dimensional scanning mirror and outputs sound wave, the wave transmission configured to be mounted integrally to the optical measurement section and output sound wave by the vibrate sections to vibrate the measurement object.

10. A measurement method of vibration of measurement object, the measurement method including:

vibrating the measurement object with sound wave output from a parametric speaker of a wave transmission section towards the measurement object;
reflecting the laser light towards the measurement object by a two-dimensional scanning mirror arranged at the center part of the sound wave output from the parametric speaker, the two-dimensional scanning mirror is provided in an optical measurement section mounted integrally to the wave transmission section;
reflecting the laser light reflected from the measurement object towards the optical measurement section by the two-dimensional scanning mirror;
making an optical axis of laser light emitted to/received from the measurement object coincident with a central axis of the sound wave output from the parametric speaker;
receiving the laser light reflected from the measurement object by the optical measurement section;
measuring vibration of the measurement object according to the received laser light by the optical measurement section.

11. The method according to claim 10, wherein the parametric speaker is arranged with a plurality of ultrasonic vibrators closely excluding the empty space section that is arranged at the center part of a polygon plane.

12. The method according to claim 11, wherein the polygon plane is regular hexagon plane.

13. The method according to claim 10, wherein the two-dimensional scanning mirror is held in the empty space section via a vibration absorbing section which absorbs vibration generated by the ultrasonic vibrators.

14. The method according to claim 10, wherein the optical measurement section comprises;

a laser light source configured to emit laser light; and
a light receiving element configured to receive the laser light reflected from the measurement object, and
the two-dimensional scanning mirror reflects the laser light from the laser light source towards the measurement object and reflects the laser light reflected from the measurement object towards the light receiving element side.

15. The method according to claim 14 further comprising:

amplifying the signal output from the light receiving element;
detecting a Doppler frequency from the signal amplified; and
displaying vibration data on a display based on the Doppler frequency.

16. The method according to claim 14, wherein the parametric speaker is arranged with a plurality of ultrasonic vibrators closely excluding the empty space section that is arranged at the center part of a polygon plane or a circular plane, the two-dimensional scanning mirror is held in the empty space section and is at a position deviated with respect to the ultrasonic vibrators in the direction orthogonal to the ultrasonic vibrators, the two-dimensional scanning mirror reflects the laser light from the laser light source in the direction parallel to the ultrasonic vibrators towards the measurement object through the empty space section.

17. The method according to claim 16, wherein the two-dimensional scanning is tilted at 45 degrees to the polygon plane.

* * * * *